US00PP23744P3

(12) United States Plant Patent
Cain

(10) Patent No.: US PP23,744 P3
(45) Date of Patent: Jul. 16, 2013

(54) GRAPEVINE 'IFG NINE'

(50) Latin Name: *Vitis vinifera*
Varietal Denomination: IFG Nine

(75) Inventor: David Cain, Bakersfield, CA (US)

(73) Assignee: International Fruit Genetics LLC, Bakersfield, CA (US)

( * ) Notice: Subject to any disclaimer, the term of this patent is extended or adjusted under 35 U.S.C. 154(b) by 10 days.

(21) Appl. No.: 13/199,228

(22) Filed: Aug. 24, 2011

(65) Prior Publication Data

US 2013/0055475 P1 Feb. 28, 2013

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para

(57) ABSTRACT

This invention is a new and distinct grapevine variety named 'IFG Nine' which is characterized by producing naturally large light red, firm, narrow ellipsoid to somewhat cylindrical seedless grapes borne on large clusters. The fruit ripen and are harvestable in early to mid-September.

1 Drawing Sheet

Latin name of the genus and species claimed: *Vitis vinifera*. Variety denomination: 'IFG Nine'.

BACKGROUND OF THE INVENTION

The new and distinct grapevine described and claimed herein originated from a hand pollinated cross of the Redglobe variety (U.S. Plant Pat. No. 4,787 expired) and the Princess variety (non-patented) hybridized in May 2001. The seeds were subsequently germinated and the resulting plants were planted in the field in April 2002. The present variety of grapevine was selected as a single plant in August 2003 and was first asexually propagated by hardwood cuttings in December 2003 near Delano, Kern County, Calif. The resulting propagules were planted during April 2004 near Delano, Kern County, Calif. and were found to reproduce true-to-type through at least three generations of asexual reproduction.

BRIEF SUMMARY OF THE INVENTION

The new grapevine 'IFG Nine' is characterized by producing naturally large, narrow ellipsoid to somewhat cylindrical, red seedless berries which ripen with or slightly before the Crimson variety. Berries have crisp texture, excellent eating quality and are able to develop bright red skin color more readily than the Crimson variety.

To the inventor's knowledge, the known varieties to which the new grapevine variety is most similar are the Crimson Variety (unpatented) and the Sheegene-1 (U.S. Plant Pat. No. 18,937). The 'IFG Nine' can be distinguished from the Crimson variety by having much larger natural berry size. The 'IFG Nine' does not require the use of gibberellic acid to attain acceptable commercial berry size while the Crimson variety requires gibberellic acid applications and/or girdling to attain acceptable size. 'IFG Nine' also colors more easily than the Crimson variety and does not require the application of ethrel or other color enhancing chemicals to attain commercially acceptable red color. The 'IFG Nine' can be distinguished from the Sheegene-1 variety by having a slightly more narrow ellipsoid to cylindrical shaped berry as opposed to the more ovate to obtuse ovate berry shape of Sheegene-1. The 'IFG Nine' has a larger and less compact cluster than the Sheegene-1. The 'IFG Nine' cluster weight is about 1592 grams and has about 255 berries per bunch as opposed to 719 grams with 155 berries per bunch for the Sheegene-1. The berry weight of 'IFG Nine' is somewhat smaller than Sheegene-1 being 6.9 to 8.4 grams per berry as opposed to about 11.4 grams for Sheegene-1.

'IFG nine' can be distinguished from its parent, the Redglobe variety by producing seedless rather than seeded berries having a smaller more narrow ellipsoid to cylindrical shape as opposed to the round shape of Redglobe. 'IFG Nine' can be distinguished from its parent the Princess variety by having red rather than white skin coloration and by its later ripening period. 'IFG Nine' can further be distinguished based on the characteristics described below.

BRIEF DESCRIPTION OF THE FIGURE

The accompanying photographic illustration in FIG. 1 illustrates in full color 'IFG Nine'. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Nine' plants grown in the vicinity of Delano, Kern County, Calif. during 2009, and 2010 and is believed to apply to plants of the variety grown under similar conditions of soil and climate elsewhere:

VINE

General:
- *Size*.—Large.
- *Vigor*.—Vigorous.
- *Density of foliage*.—Dense.
- *Productivity*.—Productive.
- *Root stock*.—Own root.
- *Training method*.—Typically spur pruned leaving 2 bud spurs.

Trunk:
- *Trunk diameter of 4-year-old vines at 30 cm above the soil line*.—5.5 cm.
- *Shape*.—Medium.
- *Straps*.—Split.
- *Surface texture*.—Medium.
- *Inner bark color*.—Can be any of the following colors; Greyed-orange; 177A and 177B.

SHOOTS

Young shoot:
- *Form of tip*.—Wide open.
- *Distribution of anthocyanin coloration of tip*.—Piping (striped).
- *Intensity of anthocyanin coloration of tip*.—Weak.
- *Density of prostrate hairs of tip*.—Medium.
- *Density of erect hairs of tip*.—Absent.
- *Color*.—144A.

Woody shoot (mature canes):
- *Shape*.—Stocky.
- *Internode length*.—Medium; About 12.4 cm.
- *Width at node*.—About 13 mm.
- *Cross section*.—Circular.
- *Surface*.—Striate.
- *Main color*.—Can be any of the following colors; Greyed Orange; 165B and C, and 172C.
- *Density of erect hairs of nodes*.—None or very sparse.
- *Density of erect hairs on internodes*.—None or very sparse.
- *Growth of axillary shoots*.—Medium; Approximately 10.6 cm.

Flowering shoot:
- *Vigor during flowering*.—Strong.
- *Attitude during flowering on shoots not tied*.—Semi-erect.
- *Color*.—Dorsal side of internodes — Green with Red stripes.
- *Color*.—Ventral side of internodes — Green with Red stripes.
- *Color*.—Dorsal side of nodes — Green with Red stripes.
- *Color*.—Ventral side of nodes — Green with Red stripes.
- *Density of prostrate hairs of nodes*.—None.
- *Density of erect hairs of nodes*.—Very sparse.
- *Density of prostrate hairs on internode*.—Sparse.
- *Density of erect hairs on internode*.—None.
- *Anthocyanin coloration of buds*.—Absent.

Tendrils:
- *Distribution on the shoot (at full flowering)*.—Discontinuous.
- *Length of tendril*.—Medium-Long; about 22 cm.
- *Thickness*.—Thick.
- *Color*.—Can be any of the following colors; Yellow-green; 144A, and 145A.
- *Form*.—Trifurcated-Quad furcated.
- *Number of consecutive tendrils*.—Up to 2.

LEAVES

Young leaves:
- *Color of upper surface of first four distal unfolded leaves*.—Copper yellow.
- *Average intensity of anthocyanin coloration of six distal leaves prior to flowering*.—Absent or very weak.
- *Density of prostrate hairs between veins (lower surface)*.—Absent.
- *Density of prostrate hairs on veins (lower surface)*.—Sparse.
- *Density of erect hairs between veins (lower surface)*.—Absent.
- *Density of erect hairs on veins (lower surface)*.—Very sparse.

Mature leaves:
- *Average length*.—About 11.6 cm.
- *Average width*.—About 14.9 cm.
- *Mature leaf size*.—Medium.
- *Shape of blade*.—Pentagonal.
- *Number of lobes*.—5.
- *Anthocyanin coloration of main veins on upper side of blade*.—Absent.
- *Mature leaf profile*.—V-shaped.
- *Blistering surface of blade upper surface*.—Weak.
- *Leaf blade tip*.—In the plane of the leaf.
- *Undulation of margin*.—Pronounced.
- *Thickness*.—Thick-Medium.
- *Undulation of blade between main and lateral veins*.—Absent.
- *Shape of teeth*.—Mixture of both sides straight and both sides convex.
- *Length of teeth*.—Short to Medium.
- *Ratio length/width of teeth*.—Small.
- *Shape of upper lateral sinuses*.—Lobes slightly overlapping.
- *Depth of upper lateral sinuses*.—Medium.
- *General shape petiole sinus*.—Lobes slightly overlapping.
- *Shape of base of upper leaf sinuses*.—V-shaped.
- *Tooth at petiole sinus*.—Present on about 50% of first emerging leaves.
- *Density of prostrate hairs between veins on lower surface of blade*.—Sparse.
- *Density if erect hairs between veins on lower surface of blade*.—Sparse.
- *Density of prostrate hairs on main veins on lower surface of blade*.—None or very sparse.
- *Density of erect hairs on main veins on lower surface of blade*.—Sparse.
- *Density of prostrate hairs on main veins on upper surface of blade*.—Sparse.
- *Density of erect hairs on main veins on upper surface of blade*.—None or very sparse.

*Autumn coloration of leaves*.—Leaves can be a single color or combination of colors, in a mottled pattern or on the edges of the leaves; Greyed-yellow; 162 A and B.

Upper surface:

*Color*.—Can be any of the following colors; Green; 137A, and B, and C.

*Anthocyanin coloration of main veins*.—Absent.

*Surface appearance*.—Semi-glossy.

*Blistering surface of blade*.—Weak.

Lower surface:

*Color*.—Can be any of the colors; Green; 144A, and 146B.

*Anthocyanin coloration of main veins* (*lower surface*).—Absent.

*Glossiness*.—Weak-Medium.

*Surface texture*.—Smooth.

*Surface appearance*.—Semi-glossy.

Petiole:

*Length*.—About 9.2 cm.

*Length of petiole compared to middle vein*.—Equal.

*Density of prostrate hairs on petiole*.—Sparse.

*Density of erect hairs on petiole*.—None.

Buds:

*Bud fruitfulness*.—Basal: Mostly fruitful.

*Position of first fruitful shoot on previous season cane*.—$1^{st}$ to $2^{nd}$ node.

*Time of bud burst*.—Late, Mar. 17, 2010.

FLOWERS

General:

*Flower sex*.—Hermaphrodite.

*Length of first inflorescence*.—Long; About 19.2 cm long by 13.0 cm wide.

*Position of first flowering and fruiting node*.—$3^{rd}$-$4^{th}$.

*Number of inflorescence per flowering shoot*.—1.1 to 2.

*Time of bloom*.—Late as compared with similar varieties in the growing area of Delano, Calif.

*Date of full bloom*.—May 18, 2010.

FRUIT

General:

*Ripening period*.—Late; Approximately Sep. 25, 2009.

*Use*.—Fresh market.

*Keeping quality*.—Good.

*Resistance to*.—Insects: Average typical of *Vitis vinifera* species. Diseases: Average typical of *Vitis vinifera* species.

*Shipping quality*.—Good.

*Refractometer test*.—Soluble solids: About 19.6 Brix.

*Brix/acid*.—About 47.5.

*Titratable acidity*.—About 0.41.

*Juice pH*.—About 4.19.

Cluster:

*Mature cluster length* (*peduncle excluded*).—About 29.1 cm.

*Mature cluster width*.—About 18.3 cm.

*Mature cluster weight*.—About 1592 g.

*Bunch density*.—Medium.

*Number of berries*.—About 255.

*Form*.—Conical.

Peduncle:

*Lignification of peduncle*.—Strong.

*Length of peduncle*.—Approximately 5.3 cm.

Berry:

*Uniformity of size*.—Uniform.

*Single berry weight*.—About 6.9 g natural; to about 8.4 g when treated with gibberellic acid.

*Shape*.—Narrow ellipsoid to somewhat cylindrical.

*Seeds*.—Absent may have an occasional noticeable seed trace.

*Cross section*.—Circular.

*Berry dimensions*.—Longitudinal axis: About 27.4 mm. Horizontal axis: About 19.7 mm.

*Berry firmness*.—Medium.

*Particular flavor*.—Neutral.

*Bloom* (*cuticular wax*).—Strong.

*Berry separation from pedicel*.—Difficult.

*Skin color* (*without bloom*).—Red-purple; 60A.

Skin:

*Thickness*.—Medium.

*Texture*.—Medium.

*Reticulation*.—Absent.

*Tenacity*.—Tenacious to flesh.

What is claimed:

1. A new and distinct variety of grapevine as herein illustrated and described.

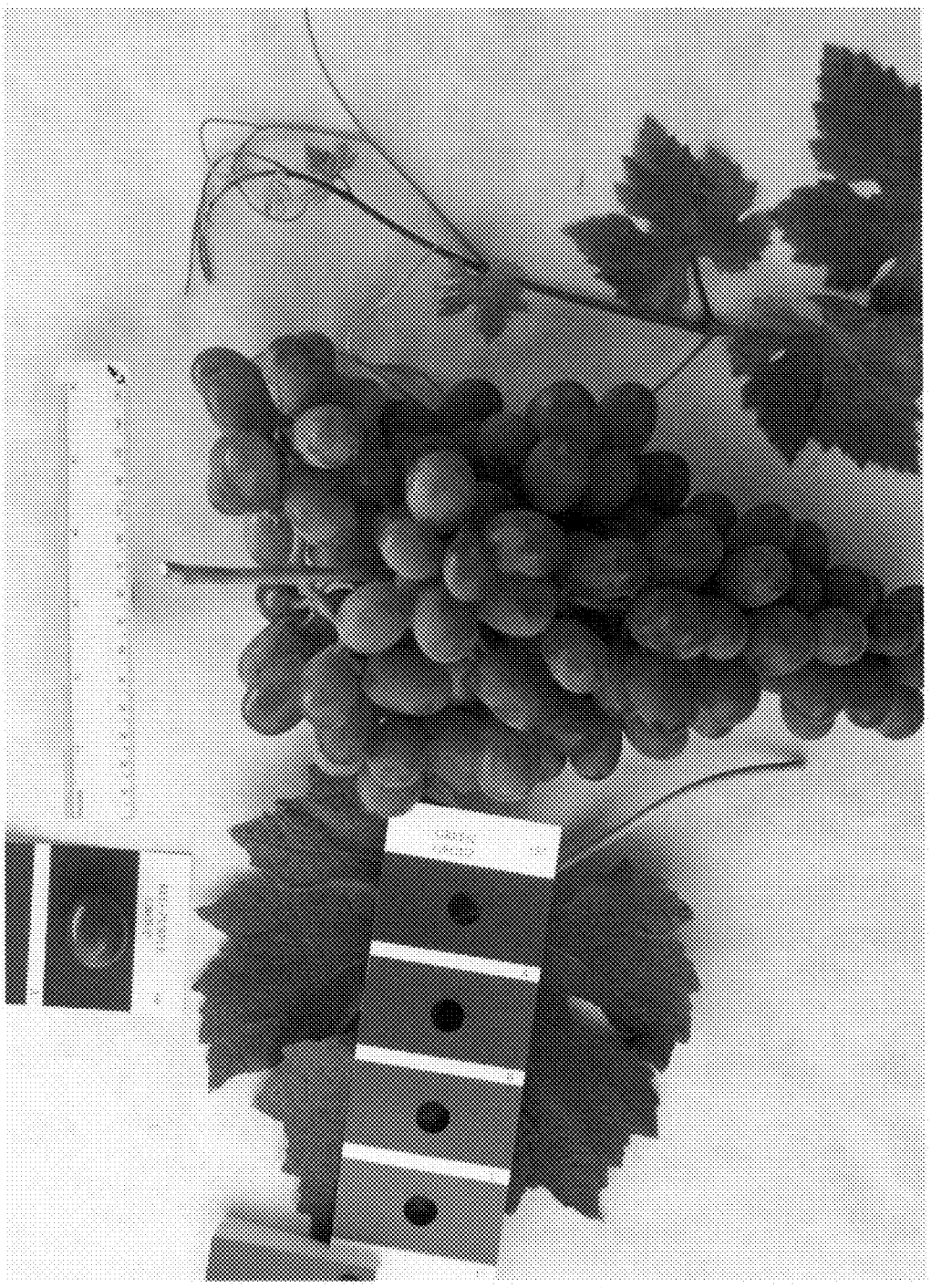

* * * * *